(12) United States Patent
Lacoste (10) Patent No.: US 9,687,682 B2
(45) Date of Patent: Jun. 27, 2017

(54) ULTRASOUND PROBE HEAD COMPRISING AN IMAGING TRANSDUCER WITH A SHIELDING ELEMENT

(75) Inventor: Francois Lacoste, Gentilly (FR)

(73) Assignee: THERACLION SA, Malakoff (FR)

( * ) Notice: Subject to any disclaimer, the term of this patent is extended or adjusted under 35 U.S.C. 154(b) by 186 days.

(21) Appl. No.: 13/698,556

(22) PCT Filed: Jun. 7, 2011

(86) PCT No.: PCT/EP2011/059401
§ 371 (c)(1),
(2), (4) Date: Jan. 22, 2013

(87) PCT Pub. No.: WO2011/157598
PCT Pub. Date: Dec. 22, 2011

(65) Prior Publication Data
US 2013/0150715 A1    Jun. 13, 2013

(30) Foreign Application Priority Data
Jun. 15, 2010 (EP) .................................... 10165937

(51) Int. Cl.
*A61B 8/00* (2006.01)
*A61N 7/02* (2006.01)
(Continued)

(52) U.S. Cl.
CPC .................. *A61N 7/02* (2013.01); *A61B 8/13* (2013.01); *A61B 8/4444* (2013.01);
(Continued)

(58) Field of Classification Search
None
See application file for complete search history.

(56) References Cited

U.S. PATENT DOCUMENTS 5,240,002 A * 8/1993 Brisson et al. ............... 600/439
5,329,928 A * 7/1994 Brisson ............. A61B 17/2258
600/439
(Continued)

FOREIGN PATENT DOCUMENTS

CN    201082314    7/2008
DE    8809253    11/1989
(Continued)

OTHER PUBLICATIONS

Hepp et al. EP 1321102, Jun. 2003. English translation.*
(Continued)

*Primary Examiner* — Jonathan Cwern
*Assistant Examiner* — Amelie R Gillman
(74) *Attorney, Agent, or Firm* — Davis & Bujold PLLC; Michael J. Bujold (57) ABSTRACT

The present invention relates to an ultrasound probe head (1), especially for HIFU treatment, comprising a treatment ultrasound transducer (2) and an imaging ultrasound transducer (3). The imaging transducer (3) comprises a shield element (4) configured such that most of the energy of ultrasound waves (10) reflected in the direction of the imaging transducer (3) are held back by said shield element (4). The shield element (4) is configured in such a way as not to interfere with the emission of the imaging ultrasound waves (7).

18 Claims, 4 Drawing Sheets

(51) Int. Cl.
*A61B 8/13* (2006.01)
*B33Y 70/00* (2015.01)
*B33Y 80/00* (2015.01)
*A61B 90/00* (2016.01)

(52) U.S. Cl.
CPC .......... *A61B 8/4483* (2013.01); *A61B 8/4494* (2013.01); *A61B 2090/378* (2016.02); *B33Y 70/00* (2014.12); *B33Y 80/00* (2014.12)

(56) References Cited

U.S. PATENT DOCUMENTS

| 5,471,988 | A | 12/1995 | Fujio et al. | |
| 5,720,287 | A | 2/1998 | Chapelon et al. | |
| 2006/0100513 | A1* | 5/2006 | Hashimoto | A61B 8/00 600/437 |
| 2006/0191344 | A1* | 8/2006 | Hashimoto | A61B 8/00 73/632 |
| 2007/0016059 | A1* | 1/2007 | Morimoto | A61B 8/4455 600/459 |
| 2008/0214964 | A1 | 9/2008 | Chapelon et al. | |
| 2009/0069688 | A1* | 3/2009 | Aono et al. | 600/459 |
| 2009/0306502 | A1* | 12/2009 | Lacoste | 600/439 |
| 2011/0140573 | A1* | 6/2011 | Crunkilton | G10K 11/004 310/322 |

FOREIGN PATENT DOCUMENTS

| DE | 202004016904 | 1/2005 |
| EP | 1321102 | 6/2003 |
| WO | 03/023760 | 3/2003 |

OTHER PUBLICATIONS

Morris, James S., Husmann, Douglas A., Wilson, W. Tad, Fulgham, Pat F., Preminger, Glenn M. "Piezoelectric v Electrohydraulic Lithotripsy: A Comparison of Morphologic Alterations." Shock Wave Lithotripsy 2: Urinary and Biliary Lithotripsy. Lingeman, James E. and Newman, Daniel M. Boston, MA: Springer US, 1989. pp. 29-33.*

* cited by examiner

ULTRASOUND PROBE HEAD COMPRISING AN IMAGING TRANSDUCER WITH A SHIELDING ELEMENT

This invention relates to an ultrasound probe head for the treatment of an organ or tissue according to claim 1, an ultrasound device according to claim 10 as well as a method of reducing damage to an imaging transducer as claimed in claim 14.

High Intensity Focused Ultrasound (HIFU) treatment may be used to destroy a target tissue or a tumor. By application of very high intensity ultrasound waves to a target area, cells are heavily damaged or destroyed. This is mainly caused by generation of heat by the ultrasound waves in the target area. Further the cavitation effect caused by the ultrasound waves as well as mechanical vibration can cause additional damage to the cells.

Typically, HIFU is ultrasound in the range of approximately 0.2 MHz to 3.5 MHz reaching an intensity of 500 W/cm$^2$ up to 50 kW/cm$^2$ at the focal point.

HIFU treatment is usually performed with a therapeutic transducer having a lens or being shaped such as to focus the treatment ultrasound waves onto a focal point. Further, it is advantageous when the therapeutic transducer in a probe head further comprises an imaging means, such as to allow an operator of the transducer to see an image of the target area. Usually, the imaging means is in the form of a diagnostic imaging ultrasound transducer, such as a b-mode ultrasound.

Probe heads with both a treatment as well as an imaging ultrasound are known in the art. For example, WO 2010/020730 and EP 2 125 112 describe such probe heads and ultrasound devices.

Usually, a coupling medium is provided between the probe head and the skin of a patient, such as to enable a high transfer efficiency of the ultrasound waves from the transducer to the tissue of the patient. Although the acoustic properties of the coupling medium as well as any cover member arranged on the probe head are kept as close as possible to the acoustic properties of human tissue, some differences in term of impedance, density and propagation speed of the ultrasound waves always exist. This leads to the reflection of a part of the ultrasound waves at the boundary coupling liquid/cover member and the skin.

One problem with known probe heads is that the reflected ultrasound waves from the treatment transducer may damage the imaging transducer. This problem is especially severe when the distance between the imaging transducer and the skin is equal to the distance from the skin to the focal point, since in this situation a maximum of reflected waves will hit the imaging transducer.

It is therefore an objective of the present invention to overcome the disadvantages of the known and specifically to provide a probe head which reduces the risk of damage to an imaging transducer by reflected treatment waves. This problem is solved by a probe head as claimed in claim 1.

The probe head of the present invention comprises:
- at least one treatment transducer for emission of ultrasound waves, preferably high intensity focused ultrasound waves focused on a focal point within or on a surface of an organ or tissue; and
- at least one imaging transducer, preferably having an imaging plane including the focal point of said treatment transducer;

According to the present invention, the imaging transducer comprises a shield element limiting the exposure of the imaging transducer to stray waves such that ultrasound waves generated by the treatment transducer reflected in the direction of the imaging transducer are at least partly held off by said shield element. Further, the shield element is designed and arranged such that ultrasound waves emitted from said imaging transducer are not obstructed by said shield element. Further, the shield element is designed and arranged such that ultrasound waves emitted from said treatment transducer are not obstructed by said shield element.

By this configuration, damages to the imaging transducer are heavily reduced, since a part of the reflected ultrasound waves of the treatment transducer are prevented from reaching the imaging transducer. It is important that the shield element is configured such as to not disturb the propagation of treatment ultrasound waves or imaging ultrasound waves travelling in the direction of the focal point. Therefore, depending on the geometry of the treatment and/or the imaging transducer, the shield element will vary in terms of its dimensions and shape.

The reflection coefficient R of sound waves at a boundary may be determined from the acoustic impedance Z of the two materials at the boundary:

$$R = \left[\frac{(Z_1 - Z_2)}{(Z_1 + Z_2)}\right]^2$$

The impedance Z is dependent on the density of the material ($\rho$) as well as the sound propagation speed ($\gamma$): $Z = \rho * \gamma$.

The amount of ultrasound waves reflected from human skin is quite considerable, which increases the risk of damage to any imaging transducer. This makes a shield element especially useful.

Further, the imaging transducer preferably has an imaging plane including the focal point of the treatment transducer. "Imaging plane" as understood herein is the plane through an organ or tissue which is being represented to an operator by means of the imaging ultrasound transducer. When the imaging transducer has an imaging plane including the focal point of the treatment transducer, it is possible to monitor the treatment and/or the position of the focal point within the tissue or organ.

The treatment transducer preferably is in the form of a spherical cap. This allows focusing of the treatment waves towards a focal point.

Preferably, at least 75%, preferably at least 85%, most preferably at least 95% of the energy of ultrasound waves from the treatment transducer reflected in the direction of the imaging transducer are held off by the shield element This ensures that the probability of damage to the imaging transducer by reflected ultrasound waves from the treatment transducer is minimized. The shield element will thereby mainly absorb or deviate the reflected high intensity ultrasound waves.

The shield element preferably is in the form of at least one wall, preferably two walls or a circumferential wall parallel or almost parallel to the ultrasound waves emitted from the imaging transducer and surrounding the active surface of the imaging transducer. "Active surface" as understood herein is meant to mean the surface of the imaging transducer actively emitting ultrasound waves, excluding any walls or other non-emitting element. The at least one wall protrudes from the active surface of the imaging transducer in the propagation direction of the imaging ultrasound waves with a height H of at least 4 mm, preferably at least 6 mm.

Providing the shield element with at least one wall allows to efficiently shield the imaging transducer from reflected ultrasound waves from the treatment transducer, as a wall has a three dimensional shape which may be configured such as to maximize the amount of energy of reflected ultrasound waves absorbed or deviated by the shield element. A circumferential wall will effectively shield the imaging transducer from reflections of all sides, especially in the case where a cup-shaped treatment transducer is used in combination with an imaging transducer arranged on the treatment transducer.

A wall with a maximal height H of at least 4 mm, preferably of 6 mm e.g. provides very good shielding of a rectangular imaging transducer with an active width of 4 mm located on a treatment transducer in the form of a half spherical cap having a diameter of 58 mm and a depth of 13.4 mm. In the case of an imaging transducer located in a spherically shaped transducer, e.g. in the form of a half spherical cap, at least two walls are needed to shield the imaging device. The spacing between these walls needs to be slightly larger than the active width of the imaging transducer, such as to provide minimal perturbation of the imaging ultrasound waves while still offering good shielding properties from treatment ultrasound waves. "Active width" as understood herein is meant to mean the width of the ultrasound emitting part of the imaging transducer, excluding the width of any wall or other non-emitting element.

The shield element preferably comprises or is made of a polymeric material, preferably an epoxy resin. More preferably the polymeric material is suitable for an additive manufacturing method, like rapid prototyping. A suitable example of such a material e.g. is DuraForm® HST Composite from 3D-systems. The materials used for the shield element must be non-transparent for ultrasound waves. Preferably, they should further allow an easy and cheap manufacturing of the shield element.

The shield element preferably has a minimal thickness of at least 0.2 mm, more preferably of at least 1 mm.

Preferably, the inner contour of the wall, viewed in a plane perpendicular to the propagation direction of the imaging ultrasound waves, has a smaller cross-section at the maximal height H of the shield element than the cross-section at the base of the shield element, which is arranged closest to the imaging transducer. This has the advantage to avoid the formation of any standing waves inside the shield element, i.e. between the walls.

Reducing the cross-section of the inner contour of the wall at the maximal height H allows maximizing the efficiency of the shield to hold off most reflected ultrasound waves from reaching the imaging transducer. However, the cross-section should not be reduced to a dimension such that the imaging ultrasound waves are hindered by the shield element, e.g. in case of two walls, depending on the emission geometry of the imaging ultrasound waves, the spacing between the walls of the shield element should not be smaller than the cross-section of the beam of imaging ultrasound waves. Most preferably, the cross-section of the inner contour of the wall matches the cross-section of the beam of imaging ultrasound waves at its maximal height H.

Further, the imaging transducer preferably is of rectangular shape, most preferably symmetrically positioned on the treatment transducer. In such a way the imaging transducer will provide for an image along most of the diameter of the treatment transducer, thus allowing monitoring the focal point as well as surrounding tissue.

The shield element is preferably provided as two wall elements positioned along the length of the imaging transducer. When the imaging transducer is of rectangular shape, it will have a width and a length. Especially in the case where the length of the imaging transducer is approximately equal to the diameter of the treatment transducer, it is not necessary to provide the shield element in the form of a circumferential wall. Rather, it is sufficient when two walls are arranged along the length of the imaging transducer. It is not necessary that the walls stretch on the entire length of the shield element and/or the imaging transducer. The length and position of the walls will depend on the shape and symmetry of the treatment ultrasound wave beam and of the expected reflections thereof. In case of a symmetrical circular treatment transducer, pointing perpendicularly to the skin of the patient, the reflected ultrasound waves will be mostly directed towards the center of the treatment transducer and hence, assuming a symmetrical position of the imaging transducer therein, also to the center of the imaging transducer.

Preferably, the at least one wall has a length of at least 6 mm, preferably of at least 10 mm for a cap-shaped circular treatment transducer with a diameter of 58 mm and a radius of curvature of 40 mm.

Alternatively, the shield element may be provided in the form of a blind covering the non-emitting parts of the imaging transducer. Further, the blind is configured such as to not disturb the imaging ultrasound waves while holding off a part of the reflected treatment ultrasound waves. This may be achieved by an appropriate outer contour and dimension of the blind. The blind may protrude from the imaging transducer in the propagation direction of the imaging ultrasound waves for a certain maximal height such that the amount of treatment ultrasound waves held off is increased, however, this maximal height will be smaller than the maximal height of the walls in the embodiments described above.

The blind may be made of or comprise a resinous material and/or glass. The material should be preferably opaque to ultrasound waves and also easily formable, e.g. by moulding or by an additive manufacturing technique, such as rapid prototyping.

The blind is preferably fixed to an ultrasound probe head. Alternatively, the blind may be configured such as to be removably attachable to an ultrasound probe head through attachment means, e.g. of the form-fit type.

Another objective of the present invention is to provide an ultrasound treatment device with a reduced risk of damage to an imaging transducer. This problem is solved by an ultrasound device according to claim 15.

The ultrasound device comprises an ultrasound probe head according to the present invention. Reflections of treatment ultrasound waves are highly reduced by the shield element arranged on the imaging transducer.

A further objective of the present invention is to provide a method to reduce damage of imaging transducers caused by reflected ultrasound waves from a treatment transducer. This problem is solved by a method according to claim 16.

The method comprises the steps of
emitting treatment ultrasound waves towards a target area, wherein a fraction of said ultrasound waves are reflected at a boundary layer
shielding the imaging transducer from said reflected ultrasound waves by means of a shield element.

The target area preferably is an organ or a tissue of a patient to be treated by ultrasound. In this case the boundary layer is the skin of the patient to be treated. Preferably, the method is carried out using a probe head according to the present invention.

Further details and embodiments of the present invention will become apparent from the following examples and figures in which.

Figure 1:
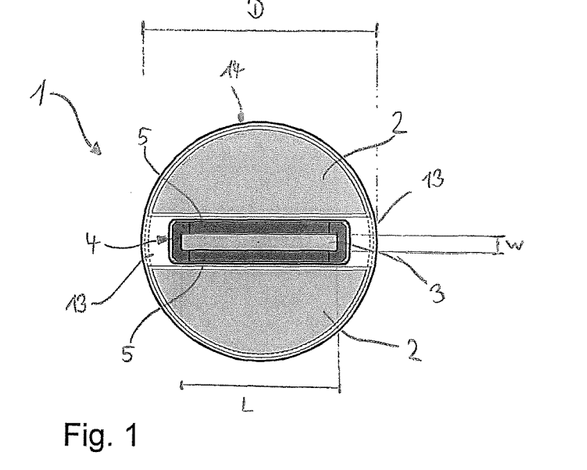
FIG. 1: shows an embodiment of a probe head according to the present invention seen from the side which faces the skin of a patient during treatment.

FIG. 1 shows one embodiment of a probe head 1 according to the present invention seen from the side which faces the skin of a patient during treatment. The probe head 1 has a circular cross-section with a diameter D and comprises a treatment transducer 2 as well as an imaging transducer 3. The treatment transducer 2 is preferably a HIFU transducer shaped as spherical cap (see also FIG. 2b). When placed on the skin of a patient, the treatment transducer 2 has a concave bending, i.e. the transducer bends away from the viewer in FIG. 1. The radius of curvature R of the treatment transducer 2, its angle of aperture $\alpha$ as well as its diameter D are selected such as to focus the ultrasound waves onto a focal point at a specific distance from the transducer in a manner known to the skilled artisan. The imaging transducer 3 is positioned symmetrically on the treatment transducer 2 and is of rectangular shape. In this embodiment, the imaging transducer 3 does not span the entire diameter D of the treatment transducer 2. As it is often sufficient to display the focal point and some surrounding tissue, it is not necessary to provide an imaging transducer 3 capable of scanning tissue along the entire diameter D of the treatment transducer 2. In this embodiment, imaging transducer 3 is flanked by flat surfaces 13 on both sides. The imaging transducer 3 is provided with a shield element 4 comprising two side walls 5 along a majority of the length L of the imaging transducer 3. No walls 5 are provided along the width W of the imaging transducer 3, as no treatment ultrasound waves will be reflected in this direction. Both transducers 2,3 are arranged in a casing 14 which may comprise further components needed for operation of the probe head, such as cooling means or electronic components.

Figure 2A:
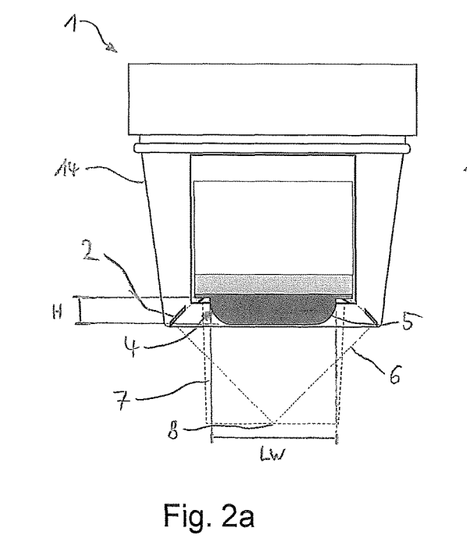
FIG. 2a: is a representation of the probe head as shown in FIG. 1 in side view.
Figure 2B:
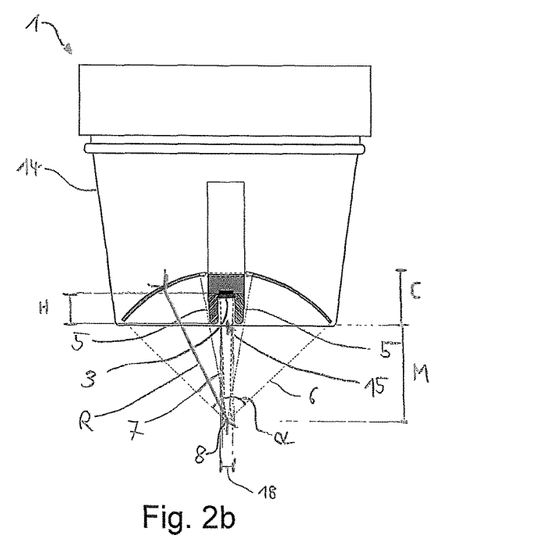
FIG. 2b: is a cross-section of the probe head as shown in FIG. 1.

FIGS. 2a and b show two side views of the probe head as shown in FIG. 1. The view in FIG. 2a is along a plane parallel to the width W of the imaging transducer 3. The treatment transducer 2 emits treatment ultrasound waves 6 focused onto a focal point 8. The imaging transducer 3 emits and receives imaging ultrasound waves 7. The imaging plane of the imaging transducer 3 includes focal point 8. The imaging transducer 3 comprises shield element 4 with two walls 5 extending generally along the length L of the imaging transducer. The shield element 4 has a maximal height H along the propagation direction of the imaging ultrasound waves 7. In this embodiment, the walls 5 are arranged on both sides of the imaging transducer along part of its length L while there are no walls along its width W. The distance of the walls at the opening is approximately equal to the width of the ultrasound beam emitted by the imaging transducer [4 mm]. Alternatively, if for example the imaging transducer has a length L which is much smaller than the diameter D of the treatment transducer 2, walls along the width W of the imaging transducer or a circumferential wall may also be provided. A circumferential wall is especially needed in case that the imaging transducer is circular in shape.

FIG. 2b is a cross-sectional side view of the probe head 1 viewed along a plane which is parallel to the length L of the imaging transducer 3. The walls 5 of the shield element 4 are arranged such as to provide an opening 15 for the imaging ultrasound waves 8. The opening 15 does not need to have a constant cross section, but may be narrower at the maximal height H, i.e. at a point which is farthest away from the imaging transducer 3, than at its base which is arranged closest to the imaging transducer 3. This may be achieved by having walls 5 provided with a curvature or with a bend as well as by arranging the walls 5 at an angle which is different from 90° to the imaging transducer 3. The imaging ultrasound wave has a width 18 at the maximal height H of the at least one wall 5. Hence, the cross-section of the inner contour of the wall 5 should be such that it is not smaller than the width 18.

For a treatment transducer 2 having a diameter D and a radius of curvature R, i.e. distance between the focal point 8 and the transducer, the angle of aperture $\alpha$ is $$\alpha = 2 \times \arcsin\left[\frac{D}{2R}\right].$$

The distance M of the focal point 8 from the casing 14 is $M = R \cos(\alpha)$ and the distance cavity C of the treatment transducer 2 is $C = R(1 - \cos(\alpha))$.

The maximal height H of the wall 5 is preferably approximated by the equation $$H \geq \frac{a}{\tan\left(\frac{\alpha}{2}\right)},$$

where a is the width 18 of the beam of imaging ultrasound waves. More preferably, the maximal height H of the wall 5 has a value $$\frac{a}{\tan\left(\frac{\alpha}{2}\right)} < H < 2\frac{a}{\tan\left(\frac{\alpha}{2}\right)}.$$

For example, for a treatment transducer 2 with a diameter D of 58 mm having a focal point 8 at 38 mm from the vertex of the transducer, the angle of aperture $\alpha$ of the spherically shaped treatment transducer 2 is 100°. The distance M of the focal point 8 from the casing 14 is 24.6 mm, since the treatment transducer 2 has a cavity C of 13.4 mm. The imaging ultrasound wave beam having a width 18 of 4 mm, the height H is between 3.3 mm and 6.7 mm.

Figure 3:
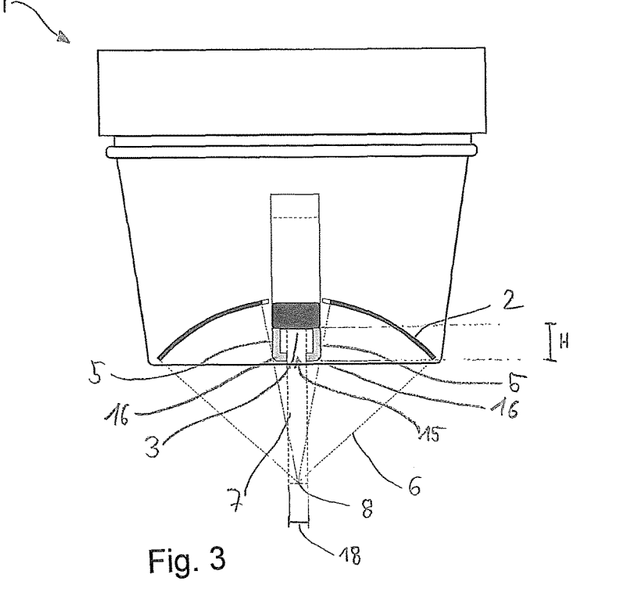
FIG. 3: shows an alternative embodiment of a probe head according to the present invention as side view.

FIG. 3 shows another exemplary embodiment of an ultrasound probe head 1 according to the present invention. In this embodiment, the walls 5 of the shielding element 4 comprise a bend 16 in the area of the maximal height H such as to narrow the opening 15. Of course, walls 5 should not be excessively bent such as to obstruct the imaging ultrasound waves 7.

Figure 4A:
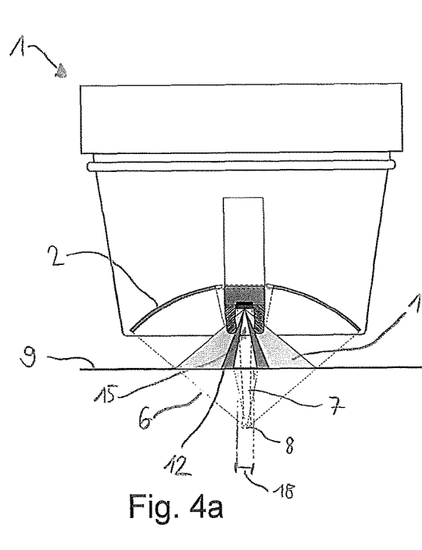
FIGS. 4a and b: is a schematic representation of the reflections of treatment ultrasound waves and the mode of action of the shield.
Figure 4B:
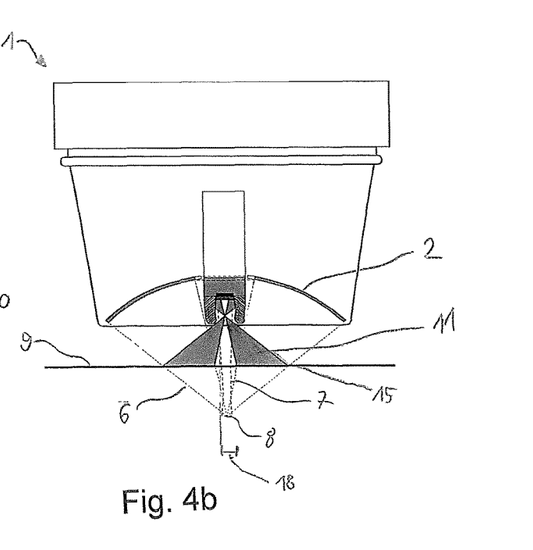

FIG. 4a and b are schematical representations of the different reflections of treatment ultrasound waves 6 on a boundary, such as skin 9. As shown in FIG. 4a, a part of the treatment ultrasound waves 6 is reflected by the skin 9. As can be seen, only a small portion of the reflected waves 12 are not held back by the walls 5 of the shield element 4 and reach imaging transducer 3. The larger portion of the reflected waves 10 will hit the walls 5 of the shield element 4 and thus do not reach the imaging transducer 3. As is shown on FIG. 4b, another portion of reflected ultrasound waves 11 will pass through opening 15 of the shield element 4, but at such an angle that their focal point is well outside of the imaging transducer 3. As can be seen, only a small fraction of these waves will actually reach the imaging transducer 3, while most will hit the walls 5 on the inside. The imaging ultrasound waves 7 are not hindered by the walls 5 of the shield element 4, since the shield element 4 and its opening 15 are configured such as to be outside of field of propagation of the imaging waves.

Figure 5:
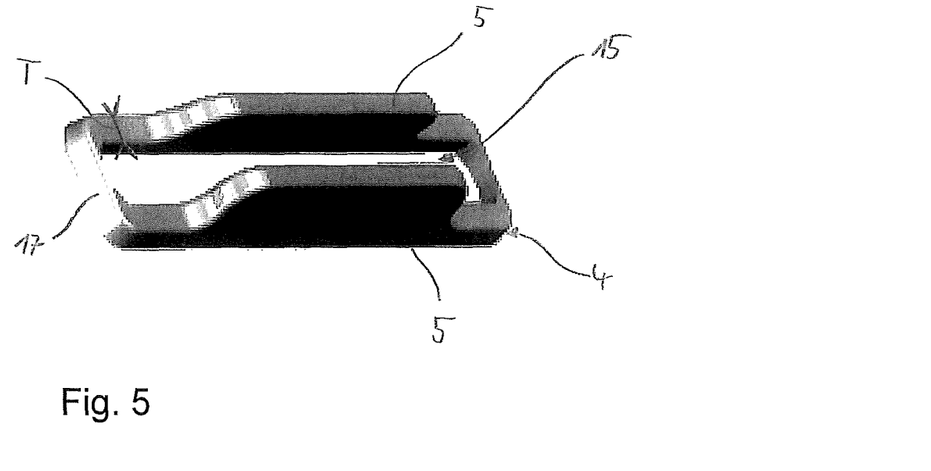
FIG. 5: shows a three dimensional representation of a shield element.

FIG. 5 is a three dimensional representation of a shield element 4 according to the present invention. As can be readily seen, the walls 5 arranged along the length L (see FIG. 1) of the imaging transducer 3 do not span the entire length L, but only a fraction of it. The shield element 4 comprises a circumferential body 17 onto which the walls 5 are arranged. In such a way it is possible to mount a shield element 4 on an existing probe head 1. Alternatively, the probe head 1 may be manufactured already equipped with a shield element 4. The body 17 has an outer contour which approximately matches the outer contour of the imaging transducer 3. The inner contour approximately matches the active portion, i.e. the area which actively emits ultrasound of the imaging transducer 3. This way the inactive portion of the imaging transducer 3 is covered and hence the shield element 5 additionally provides protection of these parts from either mechanical damage or stray high energy ultrasound. The shield element 4 has a maximal thickness T. The thickness does not need to be constant but can rather decrease, e.g. with increasing height of the walls 5. Preferably, the maximal thickness T is 1.5 mm. As can further be seen, the cross-section of the opening 15 decreases with increasing height of the walls 5. This is due to the arrangement of the walls 5 at an angle different from 90° to the plane of the imaging transducer 3. The cross-section of the opening 15 should not be smaller than the active area of the imaging transducer 3. Preferably the shield element is made of or comprises an epoxy resin and/or a metallic material.

Figure 6:
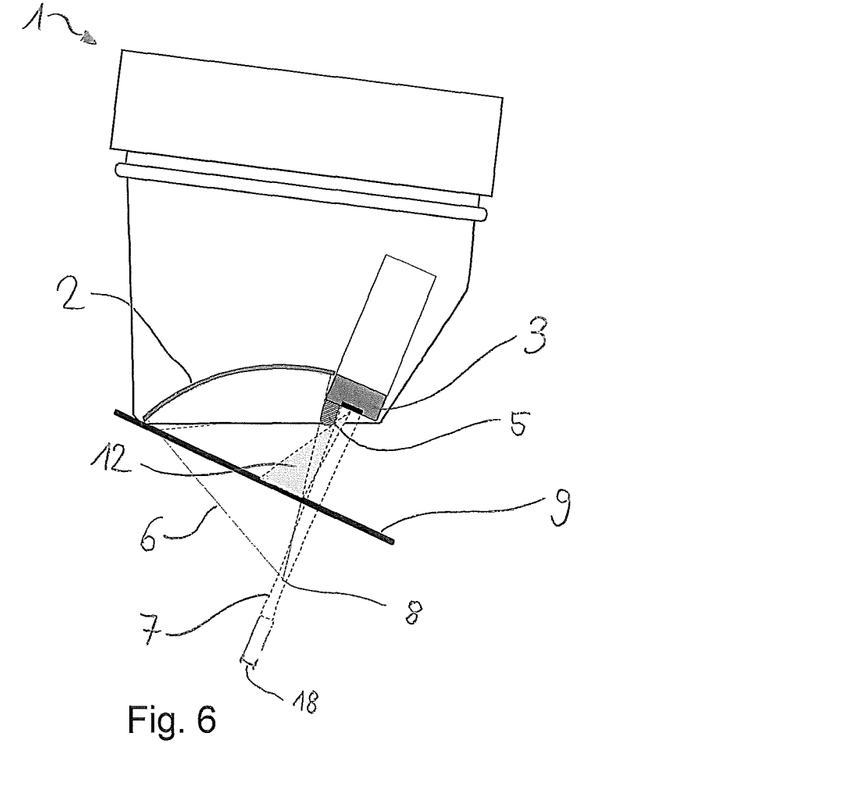
FIG. 6: shows a further embodiment of a probe head with an imaging transducer arranged asymmetrically on the treatment transducer.

FIG. 6 shows a further embodiment of an ultrasound probe head 1. In this embodiment, the imaging transducer 3 is not arranged symmetrically on treatment transducer 2, but is located on one side of it. Since reflected waves 12 may only come from the direction of the treatment transducer 2, it is sufficient to provide a shield element 4 with only one wall 5. The figure shows the situation where the biggest amount of treatment ultrasound waves 6 are reflected towards the imaging transducer 3 due to the angulation of the probe head 1 in relation to the skin 9. Fewer angulation of the probe head 1 will result in less reflected waves 12 reaching the imaging transducer 2.

Figure 7A:
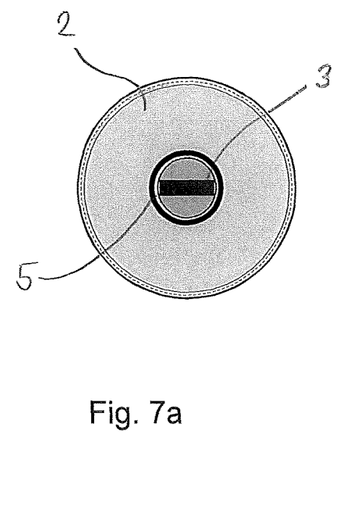
FIGS. 7a & 7b: are schematic representations of another embodiment of a probe head comprising a curved array imaging transducer, producing a fan-shaped imaging beam, with a circumferential wall.
Figure 7B:
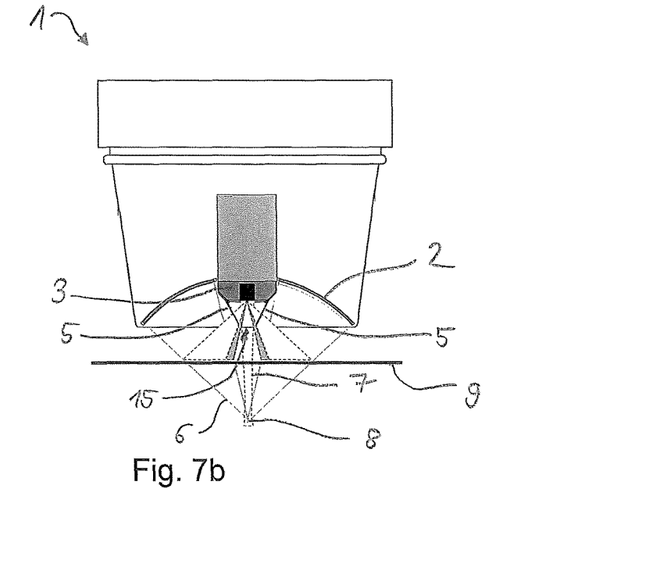

FIG. 7 is a representation of yet another embodiment of a probe head 1. In this embodiment, the imaging transducer 3 is placed symmetrically within the circular cap-like treatment transducer 2. In order to effectively shield the imaging transducer 3 from reflected waves 12, a circumferential wall 5 is needed. FIG. 7a shows the probe head 1 as seen from the side facing the skin 9 of a patient. FIG. 7b shows a cross-section of the probe head 1 along a plane which is perpendicular to the length of the imaging transducer. As can be seen, the circumferential wall 5 is configured such that the cross-section of its inner contour is smaller at its maximal height H than at the base. Such as to avoid any interference with imaging ultrasound waves 7, the height of the wall 5 may vary along its circumference.

Figure 8A:
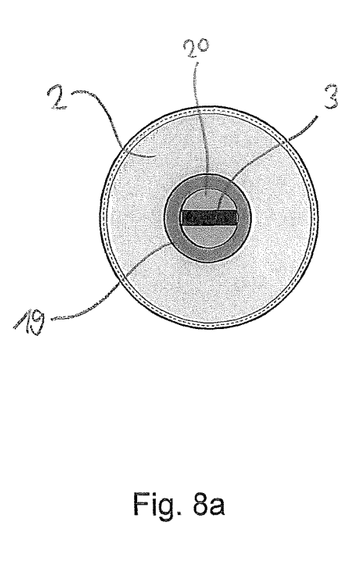
FIGS. 8a & 8b: a further embodiment of a shield element configured as blind.
Figure 8B:
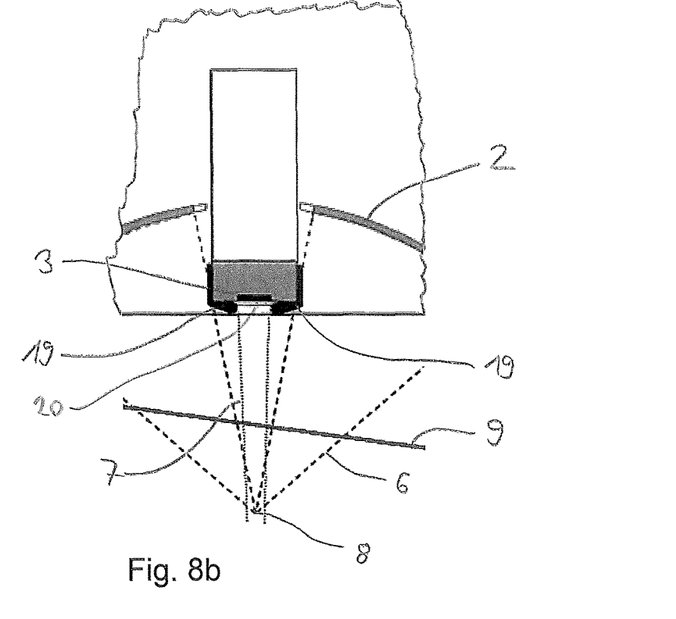

FIG. 8a shows an alternative embodiment of a probe head 1 viewed from the side of the probe head 1 facing the skin of a patient. The shield element 4 does not comprise a wall 5, but is configured as a blind 19. The blind 19 is sized and shaped such as to only cover non-emitting parts of the imaging transducer 3 while limiting the exposure of the ultrasound emitting parts of the imaging transducer 3 from reflected treatment ultrasound waves 6. While the blind 19 holds off less of the reflected treatment ultrasound waves 6 compared to the shield elements 4 with at least one wall 5, it may be used in cases where the imaging transducer 3 protrudes further into the treatment transducer 2, thereby limiting the available distance between the skin 9 and the imaging transducer 3. The blind 19 may also be adapted such as to be reversibly attachable to a probe head 1, e.g. through connection means of the form-fit type. FIG. 8b shows the same embodiment in an augmented cross-sectional view. The blind 19 has an outer surface which is not perpendicular to the imaging transducer 3. This avoids multiple reflections of the imaging ultrasound waves 7.

The invention claimed is:

1. An ultrasound probe head, for treatment of an organ or tissue, comprising:
   at least one treatment transducer for emission of therapeutic ultrasound waves having a beam with a certain width; and
   at least one imaging transducer for emission of diagnostic ultrasound waves having a beam with a certain width, wherein said at least one imaging transducer comprises an active width;
   wherein said at least one imaging transducer comprises an immovable shield element, which remains fixed in place during both the emission of diagnostic ultrasound and the emission of therapeutic ultrasound and is adapted to limit an exposure of the at least one imaging transducer such that when said therapeutic ultrasound waves generated by the at least one treatment transducer are reflected at a boundary of the organ or tissue in a direction of the at least one imaging transducer, the reflected therapeutic ultrasound waves are at least partly held off by said shield element while said diagnostic ultrasound waves emitted from said imaging transducer are not obstructed by said shield element, wherein the shield element is in the form of at least one wall, and a maximal height of the at least one wall is H, wherein $$H \geq \frac{a}{\tan\left(\frac{\alpha}{2}\right)},$$

where α is said active width of said at least one imaging transducer and α is the angle of aperture of said at least one treatment transducer, and a cross-section of an inner contour of said at least one wall, at its maximal height H, has an equal shape and an equal or bigger size than the shape and size, respectively, of said active width of said at least one imaging transducer, wherein said imaging transducer is adapted to be used to monitor the treatment of a focal point within the organ or tissue.

2. The ultrasound probe head as claimed in claim 1, wherein the at least one wall of the shield element is adapted to hold off at least 75% of the energy of the therapeutic ultrasound waves, emitted from the at least one treatment transducer, which have been reflected at the boundary in the direction of the at least one imaging transducer.

3. The ultrasound probe head as claimed in claim 1, wherein said shield element comprises or consists of a polymeric material.

4. The ultrasound probe head as claimed in claim 3, wherein the polymeric material is an epoxy resin charged with glass and/or a metallic material.

5. The ultrasound probe head as claimed in claim 1, wherein the at least one treatment transducer is in the form of a spherical cap.

6. The ultrasound probe head as claimed in claim 1, wherein the at least one imaging transducer is of rectangular shape.

7. The ultrasound probe head as claimed in claim 6, wherein the at least one imaging transducer is symmetrically positioned on the at least one treatment transducer.

8. The ultrasound probe head according to claim 1, wherein the height H of the at least one wall is at least 4 mm.

9. The ultrasound probe head as claimed in claim 1, wherein said shield element has a maximal thickness of at least 1.5 mm.

10. The ultrasound probe head as claimed in claim 1, wherein said inner contour of the at least one wall, has a smaller cross-section at the maximal height of the shield element than a cross-section at a base of the shield element.

11. The ultrasound probe head as claimed in claim 1, wherein the shield element is in the form of two walls positioned along a length of the at least one imaging transducer.

12. The ultrasound probe head as claimed in claim 1, the at least one wall has a length along a length of the at least one imaging transducer which is at least 10% of the length of the at least one imaging transducer.

13. The ultrasound probe head as claimed in claim 1, the at least one wall has a length of at least 6 mm along a length of the at least one imaging transducer.

14. The ultrasound probe head as claimed in claim 1, wherein the treatment transducer is adapted to emit said therapeutic ultrasound waves as high intensity focused therapeutic ultrasound waves focused on the focal point within or on the surface of said organ or tissue.

15. The ultrasound probe head as claimed in claim 1, wherein the at least one imaging transducer is adapted to have an imaging plane including the focal point of said at least one treatment transducer.

16. The ultrasound probe head as claimed in claim 1, wherein said at least one wall is a circumferential wall which has said maximal height H.

17. An ultrasound device comprising the ultrasound probe head as claimed in claim 1.

18. A method for reducing damage to an ultrasound imaging transducer positioned on an ultrasound treatment transducer that is caused by reflection of treatment ultrasound waves, wherein said method comprises the steps of:

emitting the treatment ultrasound waves towards a target area, wherein a fraction of said treatment ultrasound waves are reflected at a boundary, shielding the imaging transducer from said reflected treatment ultrasound waves by an immovable shield element, wherein said imaging transducer is adapted to be used to monitor the treatment of a focal point within the organ or tissue, emitting diagnostic ultrasound waves from said at imaging transducer, wherein said emitted diagnostic ultrasound waves from said at least imaging transducer are not obstructed by said shield element, wherein the shield element is in the form of at least one wall, and a maximal height of the at least one wall is H, wherein $$H \geq \frac{a}{\tan\left(\frac{\alpha}{2}\right)},$$

where α is a width of the imaging diagnostic ultrasound wave emitted from said imaging transducer and α is the angle of aperture of the treatment transducer, and a cross-section of an inner contour of the at least one wall at its maximal height H has an equal shape and an equal or bigger size than the shape and size, respectively of a cross-section of the imaging diagnostic ultrasound wave.

* * * * *